US010238280B2

(12) United States Patent
Maeda et al.

(10) Patent No.: US 10,238,280 B2
(45) Date of Patent: Mar. 26, 2019

(54) VISUAL ACUITY TEST DEVICE AND VISUAL ACUITY TEST SYSTEM

(71) Applicant: Rohm Co., Ltd., Kyoto (JP)

(72) Inventors: Toshihisa Maeda, Kyoto (JP); Masahide Tanaka, Osaka (JP)

(73) Assignee: Rohm Co., Ltd., Kyoto (JP)

( * ) Notice: Subject to any disclaimer, the term of this patent is extended or adjusted under 35 U.S.C. 154(b) by 0 days.

(21) Appl. No.: 15/547,555

(22) PCT Filed: Jan. 22, 2016

(86) PCT No.: PCT/JP2016/051765
§ 371 (c)(1),
(2) Date: Jul. 31, 2017

(87) PCT Pub. No.: WO2016/132804
PCT Pub. Date: Aug. 25, 2016

(65) Prior Publication Data
US 2018/0020910 A1    Jan. 25, 2018

(30) Foreign Application Priority Data

Feb. 17, 2015 (JP) ................................. 2015-028851

(51) Int. Cl.
*A61B 3/028* (2006.01)
*A61B 3/00* (2006.01)
*A61B 5/11* (2006.01)

(52) U.S. Cl.
CPC ............ *A61B 3/028* (2013.01); *A61B 3/0041* (2013.01); *A61B 5/11* (2013.01); *A61B 2562/0219* (2013.01)

(58) Field of Classification Search
CPC ......... A61B 3/032; A61B 3/0033; A61B 3/18; A61B 3/024; A61B 3/028; A61B 3/02
(Continued)

(56) References Cited

U.S. PATENT DOCUMENTS 4,968,131 A * 11/1990 Lewis .................... A61B 3/032
351/239
2005/0213033 A1    9/2005 Sabel
(Continued)

FOREIGN PATENT DOCUMENTS

JP    2004233880    8/2004
JP    2004-286833    10/2004
(Continued)

OTHER PUBLICATIONS

Japan Patent Office, Office Action for JP Application No. 2017-500558 dated May 22, 2018 (with English Translation).
(Continued)

*Primary Examiner* — Mohammed A Hasan
(74) *Attorney, Agent, or Firm* — Fish & Richardson P.C.

(57) ABSTRACT

A portable visual acuity examination device comprises a mounting unit that can be mounted in front of eyes either using or not using eyeglasses, a visual target displaying unit that uses an organic EL display panel, a display controlling unit that changes the visual target displayed on the displaying unit, an inputting unit for visual target viewing results, and a transmitting unit for measurement results. The portable visual acuity examination device comprises an optical system that can change the distance at which the visual target virtual image is visible. The portable visual acuity examination device detects whether eyeglasses are used and matches an uncorrected vision acuity examination and a corrected vision acuity examination. The portable visual acuity examination device switches between a C-type visual target and an E-type visual target. With data display, both the right and left display units are enabled.

20 Claims, 3 Drawing Sheets

(58) Field of Classification Search
 USPC .......................................................... 351/223
 See application file for complete search history.

(56)  References Cited

U.S. PATENT DOCUMENTS

2006/0283466 A1   12/2006  Sabel
 2007/0038142 A1*   2/2007  Todd ..................... A61B 3/024
                                                                  600/558
 2007/0182928 A1    8/2007  Sabel
 2007/0216865 A1    9/2007  Sabel et al.
 2010/0118264 A1    5/2010  Sabel
 2013/0044290 A1    2/2013  Kawamura
 2014/0118685 A1    5/2014  Kawamura
 2016/0198951 A1*   7/2016  Fujino .................. A61B 3/1005
                                                                  351/206

FOREIGN PATENT DOCUMENTS

JP      2005-296402    10/2005
 JP      2008-534157     8/2008
 JP       2011211383    10/2011
 JP      2011-224198    11/2011
 JP       2014100254     6/2014

OTHER PUBLICATIONS

Japan Patent Office, International Search Report for PCT/JP2016/051765 with English translation.

* cited by examiner

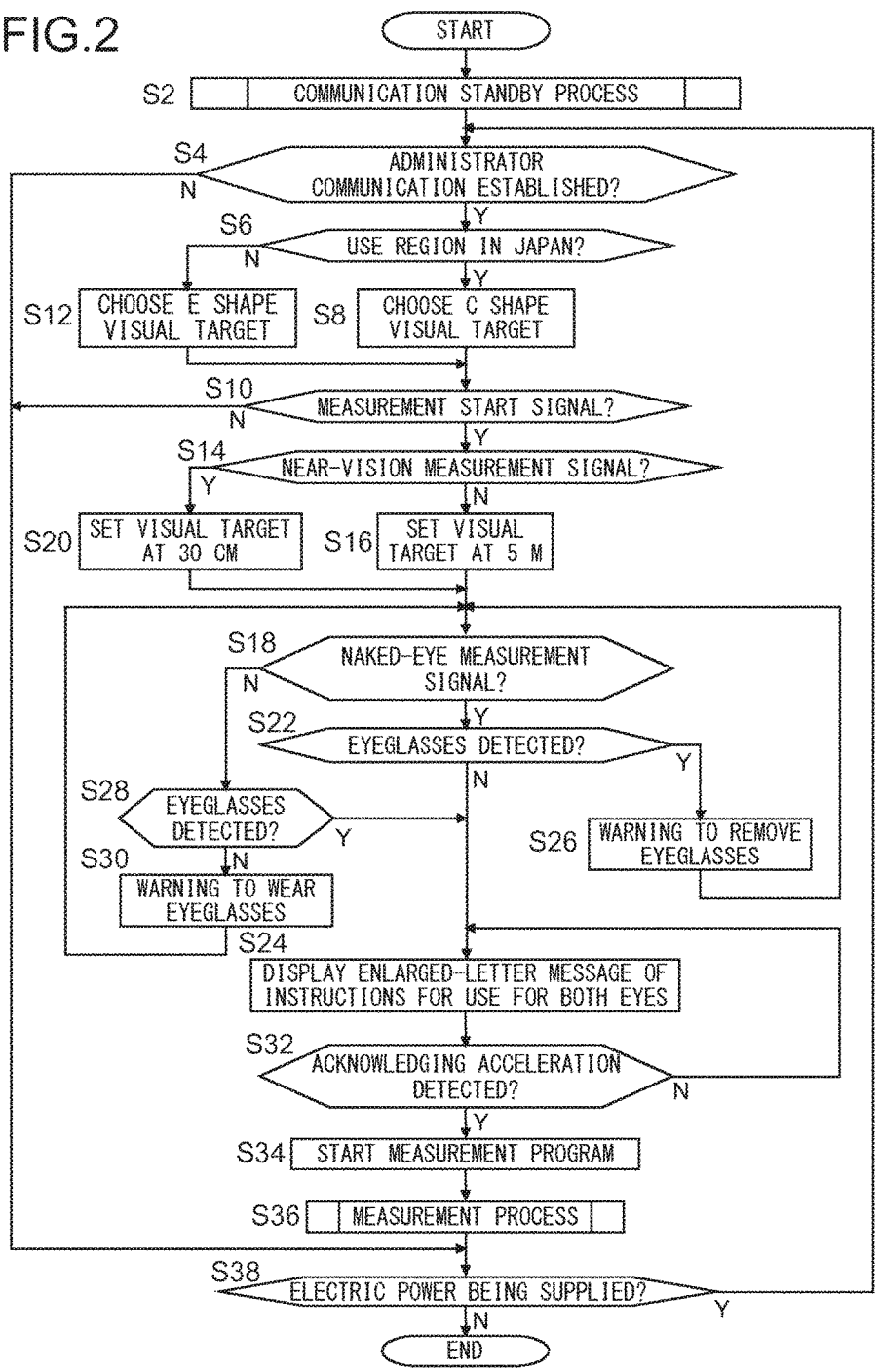

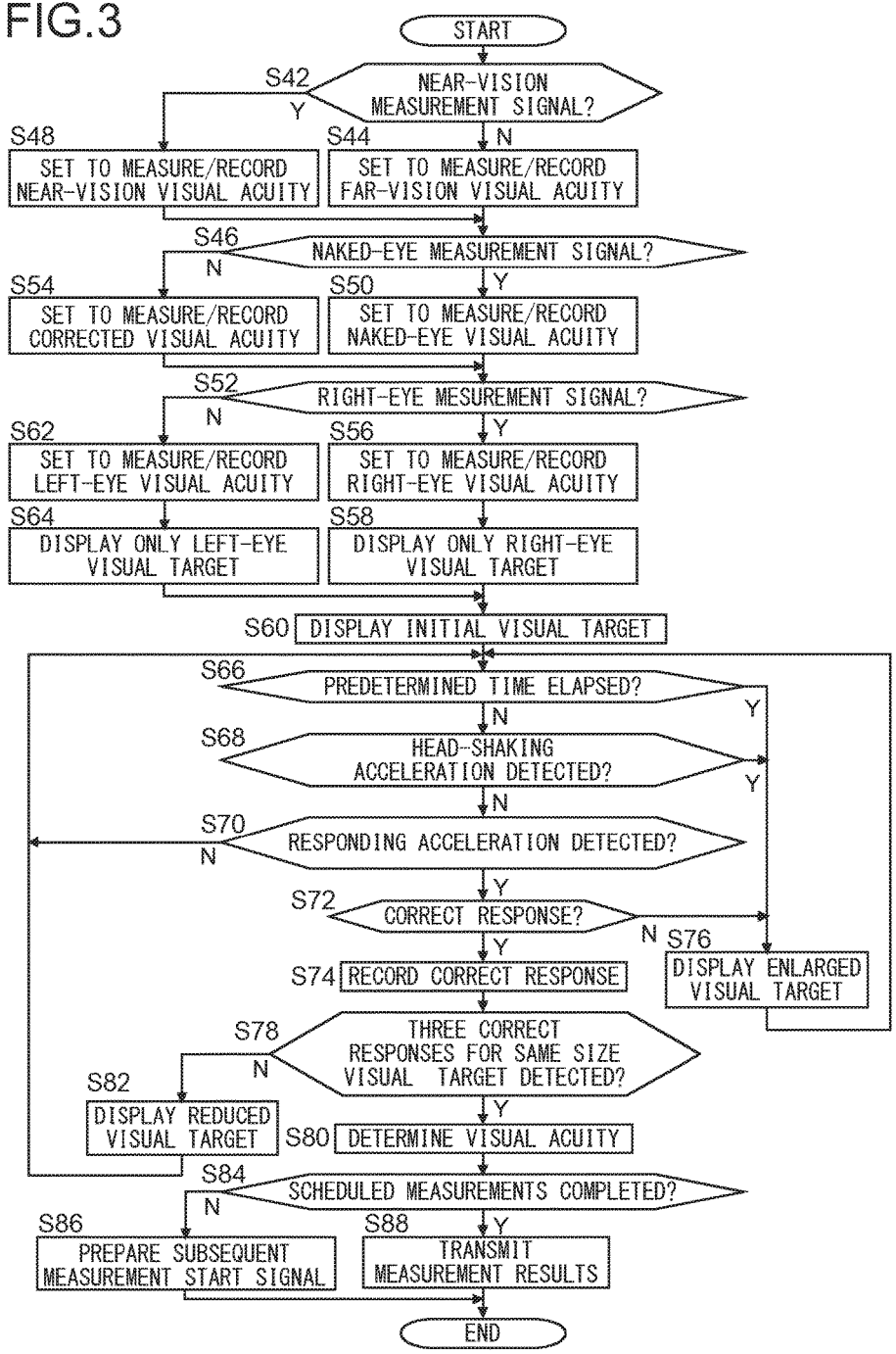

VISUAL ACUITY TEST DEVICE AND VISUAL ACUITY TEST SYSTEM

TECHNICAL FIELD

The present invention relates to a visual acuity test device and a visual acuity test system.

BACKGROUND ART

Visual acuity tests are performed by letting a subject recognize a visual acuity chart on which are displayed C shape Landolt rings, which are commonly used in Japan, or E shape letters of a Tumbling E chart, which are commonly used in the United States, etc., or alphabets in a Snellen chart. Thereby far-vision visual acuity, near-vision visual acuity, etc., are measured. Use of automatic visual acuity test devices has been proposed in which, instead of a tester letting a subject read aloud the recognition result of a visual target of a visual acuity chart pointed by the tester, a visual target is displayed in a housing into which the subject can look, and a subject by himself/herself can input the recognition result of a visual target by operating a joystick lever (Patent Document 1).

LIST OF CITATIONS

Patent Literature

Patent Document 1: JP-A-2005-296402

SUMMARY OF THE INVENTION

Technical Problem

However, there are yet many problems to be studied in relation to visual acuity test devices and visual acuity test systems.

In view of the above, an object of the present invention is to provide improved visual acuity test devices and improved visual acuity test systems.

Means for Solving the Problem

According to one feature of the present invention, a portable visual acuity test device includes a mount worn in front of an eye, a display which displays a visual target for a visual acuity test, a display controller which switches visual targets displayed on the display, an input unit to which the recognition result of a visual target is inputted, and a transmitter which transmits a measurement result. It is thereby possible to obtain a portable visual acuity test device that can be worn on a person's head.

According to a specific feature, the display comprises an organic electroluminescence display panel. It is thereby possible to achieve display of black in display of a black and white visual target.

According to another specific feature, the portable visual acuity test device includes an optical system which permits adjustment of a distance at which a virtual image of the visual target is seen. It is thereby possible to obtain a portable visual acuity test device that can measure far-vison visual acuity and near-vision visual acuity.

According to another specific feature, the mount is mountable in front of the eye both in an eyeglasses-worn state and in a naked-eye state. It is thereby possible to obtain a portable visual acuity test device that can measure naked-eye visual acuity and corrected visual acuity. According to a more specific feature, the portable visual acuity test device includes a detector which detects whether or not eyeglasses are worn. According to an even more specific feature, the detector determines a relationship between whether an intended test is a naked-eye visual acuity test or a corrected visual acuity test and whether or not eyeglasses are worn.

According to another specific feature, the display can switch between a C shape visual target and an E shape visual target. It is thereby possible to obtain a portable visual acuity test device that suits the use region.

According to another specific feature, the display has a right-eye display and a left-eye display. In a visual acuity test, one of the right-eye display and the left-eye display is enabled, and in information display, the right-eye display and the left-eye display are both enabled. It is thereby possible to obtain a portable visual acuity test device that allows smooth measurement. According to yet another specific feature, in information display, the display displays in letters enlarged to be larger than a visual target. This also helps allow smooth measurement.

According to another specific feature, the portable visual acuity test device autonomically performs a plurality of kinds of visual acuity tests. It is thereby possible to smoothly perform measurements for the right-eye, the left-eye, far-vision visual acuity, near-vision visual acuity, naked-eye visual acuity, corrected visual acuity, etc.

According to another feature of the present invention, a portable visual acuity test device includes a mount worn in front of an eye, a display which displays a visual target for a visual acuity test, and an acceleration sensor. The recognition result of a visual target is inputted by a head movement. It is thereby possible to smoothly input the recognition result, and thus to smoothly proceed from the acknowledgment of display content to a visual acuity test. According to a specific feature, the recognition result of a visual acuity is determined based on a relationship between a direction of a visual target displayed on the display and a direction of a head movement. According to another specific feature, inability to recognize is inputted by a predetermined head movement.

According to yet another feature of the present invention, a visual acuity test system includes a plurality of portable visual acuity test devices, and an administrator which can communicate with the portable visual acuity test devices. It is thereby possible to perform measurements with respect to a plurality of subjects concurrently.

Advantageous Effects of the Invention

As will be seen from the above, in accordance with the present invention, it is possible to provide improved visual acuity test devices and improved visual acuity test systems.

BRIEF DESCRIPTION OF DRAWINGS

FIG. 2 is a basic flow chart explaining the operation of an HMD controller in Example 1; and FIG. 3 is a flow chart showing the details of step S36 of FIG. 2.

DESCRIPTION OF EMBODIMENTS

Example 1

Figure 1:
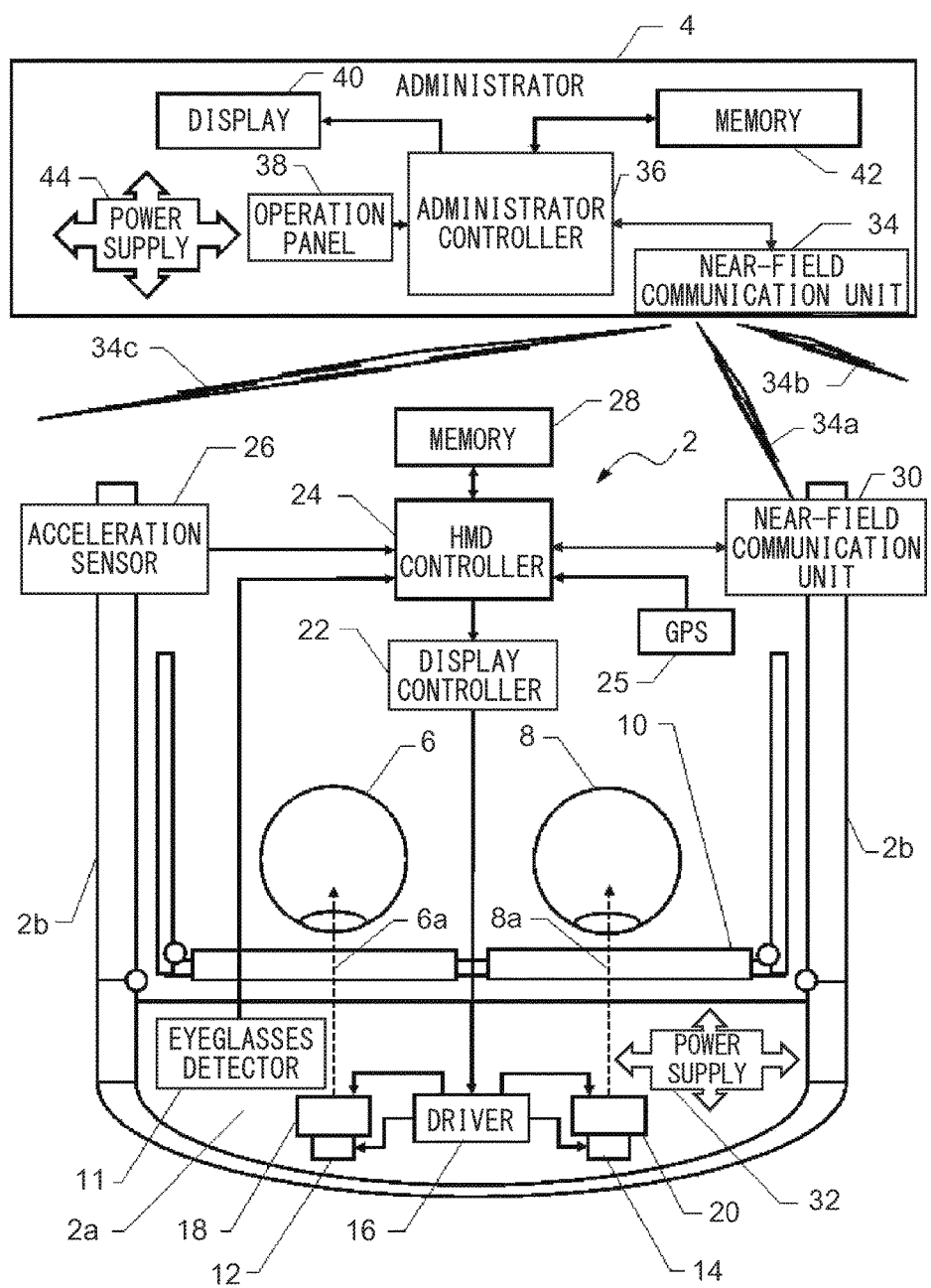
FIG. 1 is a block diagram showing the overall configuration of a visual acuity test device and a visual acuity test system in Example 1 embodying the present invention (Example 1)

FIG. 1 is a block diagram showing the overall configuration of a visual acuity test device and a visual acuity test system in Example 1 embodying the present invention. Example 1 is configured as a visual acuity test system that includes a visual acuity test device which is a google-type head-mounted portable visual acuity tester (hereinafter "portable visual acuity tester") 2 and an administrator 4 which can perform near-field communication with the portable visual acuity tester 2. Although, for the sake of simplicity, FIG. 1 shows only one portable visual acuity tester 2, the present invention is configured as a system in which a plurality of portable visual acuity testers having the same configuration are provided. The plurality of portable visual acuity testers are made capable of performing near-field communication with the administrator 4 so that visual acuity tests are concurrently performed with the portable visual acuity testers worn by a plurality of subjects on their heads respectively, and the results are transmitted to the administrator 4, and thereby it is possible to concurrently process, in the administrator 4, the results of the visual acuity tests taken by the plurality of subjects. As will be described later, the tests performed by the portable visual acuity testers are voluntarily taken by the subjects. Hereinafter, the configuration and function of the illustrated portable visual acuity tester 2 as a representative of the plurality of the portable visual acuity testers will be described together with those of the administrator 4.

The portable visual acuity tester 2 can be worn further in front of eyeglasses 10, which a subject usually wears, worn in front of the subject's right and left eyes 6 and 8, and in this state, corrected visual acuity can be measured. When the eyeglasses 10 are taken off and the portable visual acuity tester 2 alone is worn, uncorrected visual acuity can be measured. To that end, the portable visual acuity tester 2 comprises a body 2a and temples 2b, and is configured such that, when the temples 2b are placed on the ears over the eyeglasses 10, the body 2a is located in front of the lenses of the eyeglasses 10. On the other hand, when the temples 2b are placed on the ears directly without the eyeglasses 10, the portable visual acuity tester 2 is located in front of the eyes with an accommodation space left for the eyeglasses, and thus uncorrected visual acuity can be measured. In the body 2a, an eyeglasses detector 11 is provided that detects whether or not the eyeglasses 10 are present; this makes it possible to automatically distinguish between measurement of corrected visual acuity and that of uncorrected visual acuity, and also to provide a function of giving a warning that a given state is not appropriately suitable for the purpose, for example, when the eyeglasses 10 are detected in preparation for measurement of uncorrected vision (for example, a function of displaying a warning to take off the eyeglasses) or the like.

A right-eye display 12 and a left-eye display 14 inside the body 2a each comprise an OLED (organic light-emitting diode) display panel exploiting organic electroluminescence. The right-eye display 12 and the left-eye display 14 are each monochrome, and use an OLED (organic light-emitting diode) display panel, and this permits, when a black and white visual target for visual acuity test is shown with varying sizes and directions, black to appear distinct, contributing to visual acuity test.

As will be described later, a driver 16 drives selectively either the right-eye display 12 or the left-eye display 14 based on a video signal for visual target display fed from a display controller 22 to display a right-eye visual target or a left-eye visual target on its display surface. As indicated by broken-line arrows, virtual images of a visual target displayed on the display surfaces are directed to the right and left eyes 6 and 8 along lines of sight 6a and 8a by right-eye and left-eye eyepiece optical systems 18 and 20 respectively. The right-eye and left-eye eyepiece optical systems 18 and 20 adjust the distance at which the virtual images of the visual target are seen according to whether far-vision visual acuity measurement or near-vision visual acuity measurement is performed.

The portable visual acuity tester 2 further includes a head-mounted display controller (hereinafter "HMD controller") 24, a global positioning system terminal (hereinafter "GPS") 25, an acceleration sensor 26, a memory 28, and a near-field communication unit 30. The HMD controller 24 controls the various functions of the portable visual acuity testers 2 based on a program stored in the memory 28.

Now, a description will be given of the function of the HMD controller 24. First, the result of detection by the eyeglasses detector 11 is transmitted to the HMD controller 24 so that corrected or uncorrected visual acuity measurement is performed as intended as described above. Then, the HMD controller 24 transmits an optical drive signal to the driver 16 via the display controller 22, and thereby drives the right-eye and left-eye eyepiece optical systems 18 and 20 to set whether to perform far-vision visual acuity measurement or near-vision visual acuity measurement. Meanwhile, the GPS 25 detects the region where the portable visual acuity tester 2 is being used, and transmits the result of detection to the HMD controller 24 so that the visual target data to be used is automatically switched among the visual target data stored in the memory 28 such that, for example, when the use region is in Japan, a Landolt ring is displayed as a vision target, and when the use region is in the United States, a letter of the Tumbling E chart is displayed as a vision target. Then, the HMD controller 24 controls the display controller 22 based on the visual target data stored in the memory 28 with consideration also given to a signal received from the acceleration sensor 26 so as to make the driver 16 transmit a video signal for visual target display.

More specifically, the acceleration sensor 26 detects the movement of the head of a subject indicating the recognition result of a visual target, and transmits a detection signal to the HMD controller 24. For example, when the subject moves the head in any of the up/down/left/right directions in which a cut in a Landolt ring is open (for example, on recognizing a cut on the right side, the subject turns the head to the right), the acceleration sensor 26 detects the head movement, and transmits a detection signal to the HMD controller 24, and thereby the HMD controller 24 recognizes the response of the subject. On the other hand, for example, when the subject cannot visually recognize where the cut is in the Landolt ring, and repeatedly turns the head left and right, the acceleration sensor 26 detects the movement, and this let the HMD controller 24 know that the subject cannot respond. This function will be described in detail later.

The near-field communication unit 30 communicates with the administrator 4 for exchanging information related to starting of a test and transmission of test results. The arrangement of the blocks shown in FIG. 1 is illustrated merely for the sake of convenience of description and thus does not show an actual arrangement. Specifically, the display controller 22, the HMD controller 24, the acceleration sensor 26, the memory 28, and the near-field communication unit 30 are, in fact, small components mounted inside the body 2a. In the body 2a, a power supply 32 including a battery is arranged to feed electric power to components of the portable visual acuity tester 2 as mentioned above.

On the other hand, the administrator 4 has a near-field communication unit 34 for communicating, via near-field radio waves (or infrared rays) 34a, with the near-field communication unit 30 of the portable visual acuity tester 2 configured as described above. The near-field communication unit 34 can communicate also with other portable visual acuity testers (unillustrated) having a similar configuration as the portable visual acuity tester 2 by near-field radio waves (or infrared rays) 34b and 34c and the like. An administrator controller 36 in the administrator 4 controls establishment and execution of communication with the portable visual acuity testers (hereinafter, the portable visual acuity tester 2 is taken as a representative of the plurality of portable visual acuity testers), and gives the portable visual acuity tester 2 an instruction to start measurement via the near-field communication unit 34. An operation panel 38 and a display 40 are provided to allow setting and other operations for starting of the above-described measurement. The near-field communication unit 34 receives information on the result of detection from the portable visual acuity tester 2 and stores it in a memory 42. The memory 42 stores, in addition to various data including information on the result of detection, a program for the function of the administrator 4 which operates in coordination with the portable visual acuity tester 2. A power supply 44 feeds electric power to components of the administrator 4 as mentioned above.

FIG. 2 is a basic flow chart explaining the operation of the HMD controller 24 in Example 1 described above. The flow starts when electric power starts to be supplied to the portable visual acuity tester 2 by the power supply 32. At step S2, a standby process for communicating with the administrator 4 is performed, and the flow then proceeds to step S4. At step S4, whether or not communication with the administrator 4 is established is checked, and if the communication is established, the flow proceeds to step S6.

At step S6, based on detection by the GPS 25, whether or not the use region of the portable visual acuity tester 2 is in Japan is checked. If the use region is in Japan, the flow proceeds to step S8, where a Landolt ring in a C shape is chosen as a visual target, and the flow then proceeds to step S10. On the other hand, if, at step S6, it is not detected that the use region is in Japan, an assumption is made that use is made in the United States or the like, and the flow proceeds to step S12, where a letter of the Tumbling E-chart in an E shape is chosen as a visual target, and the flow then proceeds to step S10.

At step S10, whether or not there is a measurement start signal is detected. As will be described later, once the portable visual acuity tester 2 receives the first measurement start signal from the administrator 4, it autonomically performs a scheduled measurement in a predetermined order. For example, suppose that, on receipt of, at step S10, a right-eye measurement start signal as the first measurement start signal from the administrator 4, measurement operation is started and right-eye measurement is completed; then, the next time when the flow proceeds to step S10, by the autonomic operation of the HMD controller 24, left-eye measurement is started based on a left-eye measurement start signal prepared by the HMD controller 24 by itself.

If, at step S10, a measurement start signal is detected, the flow proceeds to step S14, where whether or not there is a near-vision measurement signal is detected. This near-vision measurement signal is autonomically prepared by the HMD controller 24 by itself according to the measurement schedule as initially instructed from the administrator 4. At step S10, when measurement is started based on the first measurement start signal from the administrator 4, measurement for far vision is started first, and thus, at step S14, no near-vision measurement signal is detected.

If, at step S14, no near-vision measurement signal is detected, the flow proceeds to step S16, where the right-eye and left-eye eyepiece optical systems 18 and 20 are adjusted to set the distance at which virtual images of a visual target can be seen at, for example, 5 meters so that far-vision visual acuity measurement is set, and the flow then proceeds to step S18. On the other hand, if, at step S14, a near-vision measurement signal is detected, the flow proceeds to step S20, where the right-eye and left-eye eyepiece optical systems 18 and 20 are adjusted to set the distance at which virtual images of a visual target can be seen at, for example, 30 centimeters so that near-vision visual acuity measurement is set, and the flow then proceeds to step S18.

At step S18, whether or not there is a naked-eye measurement signal is detected. This naked-eye measurement signal is autonomically prepared by the HMD controller 24 by itself according to the measurement schedule as initially instructed from the administrator 4. At step S10, when measurement is started based on the first measurement start signal from the administrator 4, measurement for naked-eye is started first, and thus, at step S18, a naked-eye measurement signal is detected.

If, at step S18, a naked-eye measurement signal is detected, the flow proceeds to step S22, where whether or not the eyeglasses 10 are detected by the eyeglasses detector 11 is checked. If there are no eyeglasses detected, a naked-eye measurement state is confirmed, and thus the flow proceeds to step S24. On the other hand, if, at step S22, detection of the eyeglasses by the eyeglasses detector 11 is confirmed, the flow proceeds to step S26, where a warning requesting removal of the eyeglasses 10 unnecessary for naked-eye measurement is displayed on each of the right-eye and left-eye displays 12 and 14, and the flow then returns to step S18. Then, the loop of steps S18, S22, and S26 is repeated until the naked-eye measurement signal is no longer detected at step S18 or the eyeglasses 10 are removed and are no longer detected at step S22.

If, at step S18, no naked-eye measurement signal is detected, corrected visual acuity measurement is assumed to be performed, and the flow proceeds to step S28. At step S28, whether or not the eyeglasses 10 are detected by the eyeglasses detector 11 is checked, and if the eyeglasses 10 are detected, a corrected visual acuity measurement state is confirmed, and thus the flow proceeds to step S24. On the other hand, if, at step S28, detection of the eyeglasses by the eyeglasses detector 11 is not confirmed, the flow proceeds to step 30, where a warning requesting wearing of the eyeglasses 10 necessary for corrected visual acuity measurement is displayed on each of the right-eye and left-eye displays 12 and 14, and the flow then returns to step S18. Then, the loop of steps S18, S28, and S30 is repeated until the naked-eye measurement signal is detected at step S18 or the eyeglasses 10 are worn and are detected at step S28.

Through the processes described above, when an intended measurement state is confirmed, the flow proceeds to step S24, where a message of instructions for use of the portable visual acuity tester 2 is displayed on each of the right-eye and left-eye displays 12 and 14, and the flow then proceeds to step S32. In this state, a person who has poor eyesight may be in a naked-eye state, and thus the message is displayed in enlarged letters so as to be visually recognized with both eyes. The same applies to the warning display at step S30, and a person who has poor eyesight may be in the naked-eye state, and thus the warning is displayed in enlarged letters so as to be visually recognized with both eyes.

At step S32, by the acceleration sensor 26, whether or not an acceleration change based on the nodding movement (repeated up/down movement) of the head of a subject indicating his/her acknowledgment of the usage is detected is checked. If, at step S32, the acknowledging acceleration is detected, the flow proceeds to step S34. On the other hand, if the acknowledging acceleration is not detected, the flow returns to step S24, and thereafter, until the acknowledging acceleration is detected, steps S24 and S32 are repeated, and the message of instructions for use continues to be displayed.

When the flow proceeds to step S34, a measurement program starts, and the flow proceeds to step S36, where a measurement process is performed. The details will be described later. When the measurement process at step S36 is completed, the flow proceeds to step S38. If, at step S4, establishment of communication with the administrator 4 cannot be confirmed, the flow immediately jumps to step S38. Also, if, at step S10, no measurement start signal is detected, the flow immediately jumps to step S38. Cases in which no measurement start signal is detected at step S10 include, in addition to a situation where a measurement start signal has not yet been received from the administrator 4, a situation where all the scheduled measurements have been completed and thus no more measurement start signal is autonomically prepared by the portable visual acuity tester 2.

At step S38, whether or not electric power continues to be supplied to the portable visual acuity tester 2 is checked. If it is confirmed that electric power is being supplied, the flow returns to step S4, and thereafter, steps S4 through S38 are repeated to perform a scheduled measurement while coping with various situation changes. On the other hand, if, at step S38, it is not confirmed that electric power is being supplied, the flow ends.

FIG. 3 is a flow chart showing the details of the measurement process at step S36 in FIG. 2. When the flow starts, at step S42, whether or not there is a near-vision measurement signal is checked. If no near-vision measurement signal is detected, a normal far-vision visual acuity measurement state is assumed, and the flow proceeds to step S44, where a setting is made to record the result of the far-vision visual acuity measurement, and the flow then proceeds to step S46. On the other hand, if, at step S42, a near-vision measurement signal is detected, the flow proceeds to step S48, where a setting is made to record the result of the near-vision visual acuity measurement, and the flow then proceeds to step S46.

At step S46, whether or not there is a naked-eye measurement signal is checked. If a naked-eye measurement signal is detected, normal naked-eye measurement is to be performed, and thus the flow proceeds to step S50, where a setting is made to record the result of the naked-eye visual acuity measurement, and the flow then proceeds to step S52. On the other hand, if, at step S46, no naked-eye measurement signal is detected, corrected visual acuity measurement is assumed to be performed, and the flow proceeds to step S54, where a setting is made to record the result of the corrected visual acuity measurement, and the flow then proceeds to step S52.

At step S52, whether or not there is a right-eye measurement signal is checked. If a right-eye measurement signal is detected, the flow proceeds to step S56, where a setting is made to record the result of the right-eye visual acuity measurement, and then to step S58, where a visual target is displayed only on the right-eye display 12, the flow then proceeding to step S60. Here, nothing is displayed on the left-eye display 14, which is thus in a dark state. On the other hand, if, at step S52, no right-eye measurement signal is detected, left-eye measurement is assumed to be performed, and the flow proceeds to step S62, where a setting is made to record the result of the left-eye visual acuity measurement, and then to step S64, where a visual target is displayed only on the left-eye display 14, the flow then proceeding to step S60. Here, nothing is displayed on the right-eye display 12, which is thus in a dark state.

At step S60, an initial visual target of a predetermined size is displayed. As this initial visual target, one based on standard visual acuity is adopted, but if there is history data of the subject, a visual target based on the latest visual acuity is adopted. Then, the flow proceeds to step S66, where whether or not a predetermined time (the time taken to assume that the subject cannot visually recognize, for example, two seconds) has elapsed since the start of display is checked. If the predetermined time has not yet elapsed, the flow proceeds to step S68, where whether or not an acceleration change based on the head-shaking movement (repeated left- and rightward movement of the head) of the subject is detected is checked. This corresponds to the subject voluntarily admitting his/her inability to recognize the visual target before the lapse of the above-mentioned predetermined time. If, at step S68, the head-shaking acceleration is not detected, the flow proceeds to step S70.

At step S70, whether or not responding acceleration is detected is checked. A responding movement that produces such acceleration is performed by a subject according to the instructions for use. For example, having found a cut in a Landolt ring at the top, the subject performs a movement involving relatively quickly moving the head slightly up and then returning the head slowly. Likewise, having found a cut in a Landolt ring at the bottom, the subject performs a movement involving relatively quickly moving the head slightly down and then returning the head slowly. Having found a cut in a Landolt ring at the right, the subject performs a movement involving relatively quickly moving the head slightly to the right and then returning the head slowly. Having found a cut in a Landolt ring at the left, the subject performs a movement involving relatively quickly moving the head slightly to the left and then returning the head slowly. If, at step S70, any such acceleration is detected, the flow proceeds to step S72. On the other hand, if, at step S70, no responding acceleration is detected, the flow returns to step S66, and thereafter, until the predetermined time has elapsed, head-shaking acceleration is detected, or responding acceleration is detected, steps S66 through S70 are repeated to receive any response.

At step S72, whether or not the detected responding acceleration coincides with the direction of the cut in the Landolt ring, that is, whether or not a correct response is detected, is checked, and if so, the flow proceeds to step S74, where the fact of the correct response is recorded along with the size of the visual target. On the other hand, if the predetermined time has elapsed at step S66, or if head-shaking acceleration is detected at step S68, or if a correct response is not detected at step S72, the flow proceeds to step S76.

At step S76, visual targets are changed, and a visual target enlarged to the next level size according to a visual acuity test criterion is displayed to permit easier recognition, and the flow returns to step S66. Thereafter, until a correct response is detected at step S72, steps S66 through S72 and step S76 are repeated, and the visual target is sequentially enlarged until it can be visually recognized.

If, at step S74, the correct response is recorded, the flow proceeds to step S78, where whether or not the correct response recorded at step S74 is the third correct response to a visual target of the same size is checked. If correct responses have not yet been detected three times, the flow proceeds to step S82, where a visual target reduced to the next level size according to the visual acuity test criterion is displayed, and the flow then returns to step S66. Thereafter, as long as, despite size reduction of the visual target, correct responses continue to be detected at step S74, steps S66 through S74, step S78, and step S82 are repeated with sequential size reduction. As long as this continues, the correct responses recorded at step S74 are correct responses to visual targets of different sizes, and thus the flow proceeds from step S78 to step S82 repeatedly.

By contrast, as a result of size reduction of the visual target at step S82, if, at step S72, a correct response can no longer be detected, the flow proceeds to step S76, where, this time, the visual target is enlarged. As a result, if, the next time the flow proceeds to step S72, a correct response is detected, the correct response can be a correct response to a visual target having the same size as that of the visual target to which the correct response was detected previously. As a result of the visual target being repeatedly enlarged or reduced around the size of the limit of visual recognition in this way, if, at step S78, it is recognized that correct responses have been detected three times to visual targets of the same size, the flow proceeds to step S80, where the visual acuity is determined based on the size of the visual targets to which correct responses have been detected three times, and the flow then proceeds to step S84.

At step S84, whether or not all the scheduled measurements have been completed based on the instructions from the administrator 4 is checked. Then, if there is an uncompleted measurement, the flow proceeds to step S86, where a subsequent measurement start signal is prepared, and the flow then ends. As a result, the flow returns, via step S38 in FIG. 2, to step S4, and if a subsequent measurement start signal is detected at step S10, the flow proceeds, through the intervening steps, to step S36, and measurement proceeds according to the flow in FIG. 3. For example, in FIG. 3, right-eye measurement is completed, and a measurement start signal for left-eye measurement is prepared at step S86; then, in FIG. 2, when the flow reaches step S10 again, the measurement start signal for left-eye measurement is detected, and the flow then proceeds again to step S36, where a measurement process for the left-eye is performed. On the other hand, if, at step S84, it is detected that all the scheduled measurements have been completed, the flow proceeds to step S88, where the results of all the measurements are transmitted to the administrator 4, and the flow then ends. In this case, no subsequent measurement start signal is prepared, and thus even when the flow returns to step S10 in FIG. 2, the flow immediately proceeds to step S38, where the portable visual acuity tester 2 ends the autonomic measurement. The potable visual acuity tester 2 then waits to receive a subsequent measurement start signal.

The above-described various features and advantages of the present invention are not limited to those specifically described by way of a practical example above. For example, the instructions for use at step S24 and the warnings at step S26 and at step S30 are not limited to those visually displayed like the ones mentioned in the practical example. For example, a configuration may be adopted in which an earphone is provided in the portable visual acuity tester 2 so that, by driving the earphone by the HMD controller 24, instructions and warnings are given with a voice that can be heard only by a subject.

Although, in the practical example, the C shape visual target and the E shape visual target are automatically switched with each other by the GPS 25, it is also possible to adopt a configuration where, instead of a GPS or the like being provided in the portable visual acuity tester 2, visual targets are switched according to instructions from the administrator 4. Although, in the practical example, the communication between the administrator 4 and the portable visual acuity tester 2 is performed wirelessly, the communication may be performed on a wired basis. With a wired cable, electric power can be supplied across it; this makes it possible to adopt a configuration in which electric power is supplied via the cable from the power supply 44 of the administrator 4 without any power supply or the like provided in the portable visual acuity tester 2.

<Synopsis>

To follow is a comprehensive description of the various features disclosed herein.

A feature disclosed in the present specification provides a portable visual acuity test device including a mount worn in front of an eye, a display which displays a visual target for a visual acuity test, a display controller which switches visual targets displayed on the display, an input unit to which the recognition result of a visual target is inputted, and a transmitter which transmits a measurement result. It is thereby possible to obtain a portable visual acuity test device that can be worn on a person's head.

According to a specific feature, the display comprises an organic electroluminescence display panel. It is thereby possible to achieve display of black in display of a black and white visual target.

According to another specific feature, the portable visual acuity test device includes an optical system which permits adjustment of a distance at which a virtual image of the visual target is seen. It is thereby possible to obtain a portable visual acuity test device that can measure far-vison visual acuity and near-vision visual acuity.

According to another specific feature, the mount is mountable in front of the eye both in an eyeglasses-worn state and in a naked-eye state. It is thereby possible to obtain a portable visual acuity test device that can measure naked-eye visual acuity and corrected visual acuity. According to a more specific feature, the portable visual acuity test device includes a detector which detects whether or not eyeglasses are worn. According to an even more specific feature, the detector determines a relationship between whether an intended test is a naked-eye visual acuity test or a corrected visual acuity test and whether or not eyeglasses are worn.

According to another specific feature, the display can switch between a C shape visual target and an E shape visual target. It is thereby possible to obtain a portable visual acuity test device that suits the use region.

According to another specific feature, the display has a right-eye display and a left-eye display. In a visual acuity test, one of the right-eye display and the left-eye display is enabled, and in information display, the right-eye display and the left-eye display are both enabled. It is thereby possible to obtain a portable visual acuity test device that allows smooth measurement. According to yet another specific feature, in information display, the display displays in letters enlarged to be larger than a visual target. This also helps allow smooth measurement.

According to another specific feature, the portable visual acuity test device autonomically performs a plurality of kinds of visual acuity tests. It is thereby possible to smoothly perform measurements for the right-eye, the left-eye, far-vision visual acuity, near-vision visual acuity, naked-eye visual acuity, corrected visual acuity, etc.

Another feature disclosed in the present specification provides a portable visual acuity test device including a mount worn in front of an eye, a display which displays a visual target for a visual acuity test, and an acceleration sensor. The recognition result of a visual target is inputted by a head movement. It is thereby possible to smoothly input the recognition result, and thus to smoothly proceed from the acknowledgment of display content to a visual acuity test. According to a specific feature, the recognition result of a visual acuity is determined based on a relationship between a direction of a visual target displayed on the display and a direction of a head movement. According to another specific feature, inability to recognize is inputted by a predetermined head movement.

Yet another feature disclosed in the present specification provides a visual acuity test system including a plurality of portable visual acuity test devices, and an administrator which can communicate with the portable visual acuity test devices. It is thereby possible to perform measurements with respect to a plurality of subjects concurrently.

Yet another feature disclosed in the present specification provides a portable visual acuity test device including a right-eye display and a left-eye display. In a visual acuity test, one of the right-eye display and the left-eye display is enabled, and in information display, the right-eye display and the left-eye display are both enabled. It is thereby possible to appropriately test visual acuity for the right and left eyes individually, and to enhance the communicating ability by use of both eyes for the purpose of information communications.

According to a specific feature, in information display, the right-eye display and the left-eye display in letters enlarged to be larger than a visual target. It is thereby possible also to enhance the ability to communicate information, and thus to achieve smooth measurement.

According to a specific feature, the portable visual acuity test device includes an acceleration sensor. The information display and display for the visual acuity test are switched by a head movement. It is thereby possible to smoothly proceed from the acknowledgement of information display to a visual acuity test.

INDUSTRIAL APPLICABILITY

The present invention is applicable to visual acuity test devices.

LIST OF REFERENCE SIGNS

2*b* mount
12, 14 display
22 display controller
26 input unit
30 transmitter
18, 20 optical system
11 detector
26 acceleration sensor

The invention claimed is:

1. A portable visual acuity test device for a person being tested comprising:

a mount arranged to have the portable visual acuity test device worn in front of an eye of the person;

a display which displays a visual target in front of the eye of the person for a visual acuity test who wears the portable visual acuity test device;

a display controller which switches visual targets displayed on the display for the person to recognize the visual target;

an input unit to which a recognition result of the visual target is inputted by the person if the person can recognize the visual target with his/her visual activity; and a transmitter which transmits the recognition result inputted by the person to an administrator outside the portable visual acuity test device.

2. The portable visual acuity test device of claim 1, wherein the display comprises an organic electroluminescence display panel.

3. The portable visual acuity test device of claim 1, further comprising:

an optical system which permits adjustment of a distance at which a virtual image of the visual target is seen.

4. The portable visual acuity test device of claim 1, wherein the mount is arranged to have the portable visual acuity test device worn in front of the eye both in an eyeglasses-worn state and in a naked-eye state.

5. The portable visual acuity test device of claim 4, further comprising:

a detector which detects whether or not eyeglasses are worn.

6. The portable visual acuity test device of claim 5, wherein the detector determines a relationship between an intended test of a naked-eye visual acuity test and a corrected visual acuity test with eyeglasses are worn.

7. The portable visual acuity test device of claim 1, wherein the display can switch between a C shape visual target and an E shape visual target.

8. The portable visual acuity test device of claim 1, wherein
the display has a right-eye display and a left-eye display,
in a visual acuity test, one of the right-eye display and the left-eye display is enabled, and
in information display, the right-eye display and the left-eye display are both enabled.

9. The portable visual acuity test device of claim 1, wherein in information display, the display displays in letters enlarged to be larger than a visual target.

10. The portable visual acuity test device of claim 1, wherein
the input unit includes an acceleration sensor arranged to detect a head movement, wherein
the input unit inputs the recognition result of the visual target om accordance with the head movement detected by the acceleration sensor.

11. The portable visual acuity test device of claim 10, wherein the recognition result of the visual target is determined based on a relationship between a direction of the visual target displayed on the display and a direction of the head movement detected by the acceleration sensor.

12. The portable visual acuity test device of claim 10, wherein inability to recognize is inputted by a predetermined head movement detected by the acceleration sensor.

13. The portable visual acuity test device of claim 1, wherein a plurality of kinds of visual acuity tests are performed automatically.

14. A portable visual acuity test device for a person being tested comprising:

a mount arranged to have the portable visual acuity test device worn in front of an eye of the person;

a display which displays a visual target in front of the eye of the person for a visual acuity test who wears the portable visual acuity test device; and an acceleration sensor which detects a head movement of the person, wherein a recognition result of the visual target by the person is inputted by the head movement detected by the acceleration sensor, wherein the head is moved by the person toward a direction corresponding to the recognition result if the person can recognize the visual target with his/her visual activity.

15. The portable visual acuity test device of claim 14, wherein a recognition result of the visual acuity is determined based on a relationship between a direction of a visual target displayed on the display and a direction of the head movement detected by the acceleration sensor.

16. The portable visual acuity test device of claim 14, wherein inability to recognize is inputted by a predetermined head movement detected by the acceleration sensor.

17. A visual acuity test system comprising:

a plurality of portable visual acuity test devices as claimed in claim 1; and an administrator which can communicate with the portable visual acuity test devices.

18. A portable visual acuity test device for a person being tested comprising:

a mount arranged to have the portable visual acuity test device worn in front of a right-eye and a left-eye of the person;

a right-eye display which displays a visual target in front of the right-eye of the person for a right-eye visual acuity test who wears the portable visual acuity test device;

a left-eye display which displays a visual target in front of the left-eye of the person for a left-eye visual acuity test of the person; and a display controller which enables, in the visual acuity test, one of the right-eye display and the left-eye display to individually test one of the right-eye and left-eye, wherein the display controller further enables, in information display to inform the person of message of instructions or warning for use of the portable visual activity test device, both the right-eye display and the left-eye display by means of displaying the same information so that a person who has poor eyesight with singly eye may visually recognize the message of instructions or warning with complimentary visual acuities of both eyes.

19. The portable visual acuity test device of claim 18, wherein in information display, the right-eye display and the left-eye display in letters enlarged to be larger than a visual target.

20. A The portable visual acuity test device of claim 18, further comprising:

a right-eye display and a left-eye display, wherein in a visual acuity test, one of the right-eye display and the left-eye display is enabled, and in information display, the right-eye display and the left-eye display are both enabled; and an acceleration sensor which detects a head movement, wherein the information display and display for the visual acuity test are switched by the head movement detected by the acceleration sensor.

* * * * *